US006582660B1

(12) United States Patent
Heller et al.

(10) Patent No.: US 6,582,660 B1
(45) Date of Patent: *Jun. 24, 2003

(54) CONTROL SYSTEM FOR ACTIVE PROGRAMMABLE ELECTRONIC MICROBIOLOGY SYSTEM

(75) Inventors: Michael J. Heller, Encinitas, CA (US); Eugene Tu, San Diego, CA (US)

(73) Assignee: Nanogen, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/859,644

(22) Filed: May 20, 1997

Related U.S. Application Data

(63) Continuation of application No. 08/304,657, filed on Sep. 9, 1994, now Pat. No. 5,632,957, which is a continuation-in-part of application No. 08/271,882, filed on Jul. 7, 1994, now Pat. No. 6,017,696, which is a continuation-in-part of application No. 08/146,504, filed on Nov. 1, 1993, now Pat. No. 5,605,662.

(51) Int. Cl.[7] ............................ G01N 1/00; G01N 15/00; G01N 33/53; C12Q 1/68
(52) U.S. Cl. ............................ 422/68.1; 422/50; 435/6; 435/7.1; 436/501
(58) Field of Search ...................... 422/50, 68.1; 435/6, 435/91.2, 7.1, 810; 436/501; 935/77, 78, 88, 85

(56) References Cited

U.S. PATENT DOCUMENTS

| 3,950,738 A | | 4/1976 | Hayashi et al. |
| 3,995,190 A | | 11/1976 | Salgo |
| 4,283,773 A | * | 8/1981 | Daughton et al. ......... 364/900 |

(List continued on next page.)

FOREIGN PATENT DOCUMENTS

| EP | 0228075 | 7/1987 |
| GB | 2156074 | 10/1985 |
| WO | 8603782 | 7/1986 |
| WO | WO88/08528 | 11/1988 |

(List continued on next page.)

OTHER PUBLICATIONS

Anand and Southern "Pulsed Field Gel Electrophoresis," *Gel Electrophoresis of Nucleic Acids—A Practical Approach*, 2d. Ed., D. Rickwood and B.D. Hames (New York:IRL Press 1990), pp 101–123.

Anderson and Young, "Quantitative Filter Hybridization," *Nucleic Acid Hybricization—A Practical Approach*, Eds., B.D. and Hames and S.J. Higgins (Washington, D.C. :IRL Press 1985) pp 73–111.

Baines, "Setting a Sequence to Sequence a Sequence," *Bio/Technology*, 10:757–758 (1992).

(List continued on next page.)

*Primary Examiner*—Ardin H. Marschel
(74) *Attorney, Agent, or Firm*—O'Melveny & Myers LLP

(57) ABSTRACT

A system for performing molecular biological diagnosis, analysis and multi-step and multiplex reactions utilizes a self-addressable, self-assembling microelectronic system for actively carrying out controlled reactions in microscopic formats. These reactions include most molecular biological procedures, such as nucleic acid hybridization, antibody/antigen reaction, and clinical diagnostics. Multi-step combinatorial biopolymer synthesis may be performed. A controller interfaces with a user via input/output devices, preferably including a graphical display. Independent electronic control is achieved for the individual microlocations. In the preferred embodiment, the controller interfaces with a power supply and interface, the interface providing selective connection to the microlocations, polarity reversal, and optionally selective potential or current levels to individual electrodes. A system for performing sample preparation, hybridization and detection and data analysis integrates multiple steps within a combined system.

23 Claims, 13 Drawing Sheets

U.S. PATENT DOCUMENTS

| | | | |
|---|---|---|---|
| 4,563,419 A | | 1/1986 | Ranki et al. |
| 4,580,895 A | | 4/1986 | Patel |
| 4,584,075 A | | 4/1986 | Goldstein |
| 4,594,135 A | | 6/1986 | Goldstein |
| 4,751,177 A | | 6/1988 | Stabinsky |
| 4,787,963 A | | 11/1988 | MacConnell |
| 4,807,161 A | * | 2/1989 | Comfort et al. ............ 364/550 |
| 4,816,418 A | | 3/1989 | Mack et al. |
| 4,822,566 A | | 4/1989 | Newman |
| 4,908,112 A | | 3/1990 | Pace |
| 5,063,081 A | | 11/1991 | Cozzette et al. |
| 5,075,077 A | | 12/1991 | Durley, III et al. |
| 5,096,807 A | | 3/1992 | Leaback |
| 5,125,748 A | | 6/1992 | Bjornson et al. |
| 5,126,022 A | | 6/1992 | Soane et al. |
| 5,143,854 A | | 9/1992 | Pirrung et al. |
| 5,164,319 A | | 11/1992 | Hafeman et al. |
| 5,166,063 A | | 11/1992 | Johnson |
| 5,200,051 A | | 4/1993 | Cozzette et al. |
| 5,202,231 A | | 4/1993 | Drmanac et al. |
| 5,219,726 A | | 6/1993 | Evans |
| 5,227,265 A | | 7/1993 | DeBoer et al. |
| 5,234,566 A | | 8/1993 | Osman et al. |
| 5,304,487 A | | 4/1994 | Wilding et al. |
| 5,312,527 A | | 5/1994 | Mikkelsen et al. |
| 5,434,049 A | | 7/1995 | Okano et al. |

FOREIGN PATENT DOCUMENTS

| | | |
|---|---|---|
| WO | WO89/01159 | 2/1989 |
| WO | 8910977 | 11/1989 |
| WO | 9001564 | 2/1990 |
| WO | WO92/04470 | 3/1992 |
| WO | WO93/22678 | 11/1993 |
| WO | WO95/07363 | 3/1995 |
| YU | 57087 | 8/1990 |

OTHER PUBLICATIONS

Barinaga, "Will 'DNA Chip' Speed Genome Initiative?", *Science*, 253:1489 (1991).

Beattie et al., "Genosensor Technology," *The 1992 San Diego Conference: Genetic Recognition*, pp 1–5 (Nov., 1992).

Beltz et al., "Isolation of Multigene Families and Determination of Homologies by Filter Hybridization Methods," *Methods in Enzymology*, 100:266–285 (1983).

Connor et al., "Detection of Sickle Cell $\beta^3$–Globin Allele by Hybridization With Synthetic Oligonucleotides," *Proc. Natl. Acad. Sci. USA*, 80:278–282 (1983).

Drmanac et al., "Sequencing of Megabase Plus DNA by Hybridization: Theory of the Method," *Genomics*, 4:114–128 (1989).

Drmanac et al., "DNA Sequence Determination by Hybridixation: A Strategy for Efficient Large–Scale Sequencing," *Science*, 260: 1649–1652 (1993).

Fodor et al., "Multiplexed Biochemical Assays With Biological Chips," *Nature*, 364:555–556 (1993).

Fodor et al., "Light–Directed, Spatially Addressable Parallel Chemical Synthesis," *Science*, 251:767–773 (1992).

Horejsi, "Some Theoretical Aspects of Affinity Electrophoresis," *Journal of Chromatography*, 178:1–13 (1979).

Horjsi et al., Determination of Dissociation Constants of Lectin Sugar Complexes by Means of Affinity Electrophoresis, *Biochimica at Biophysica Acta*, 499:200–300 (1977).

Ranki et al., "Sandwich Hybridization as a Convenient Method for the Detection of Nucleic Acids in Crude Samples," *Gene*, 21:77–85 (1983).

Saiki, "Amplification of Genomic DNA," *PCR Protocols: A Guide to Methods and Applications*, (Academic Press, Inc. 1990), pp 13–20.

Southern et al., "Analyzing and Comparing Nucleic Acid Sequences by Hybridization to Arrays of Oligonucleotides Evaluation Using Experimental Models," *Genomics*, 13:1008–1017 (1992).

Strezoska et al., "DNA Sequencing by Hybridization: 100 Bases Read by a Non–Gel–Based Method", *Proc. Natl. Acad. Sci. USA*, 88:10089–93 (1991).

Wallace et al., "Hybridization of Synthetic Oligodcoxyribonucleotides to $\phi$×174 DNA: The Effect of Single Base Pair Mismatch," *Nucleic Acid Res.*, 6:3543–3557 (1979).

Washizu, "Electrostatic Manipulation of Biological Objects," *Journal of Electrostatics*, 25:109–123 (1990).

Washizu and Kurosawa, "Electrostatic Manipulation of DNA in Microfabricated Structures," *IEEE Transactions on Industry Applications*, 26:1165–1172 (1990).

Brown et al., "Electrochemically Induced Adsorption of Radio–Labelled DNA on Gold and HOPG Substrates for STM Investigations", *Ultramicroscopy*, 38 (1991) pp 253–264.

Palacek, "New Trends in Electrochemical Analysis of Nucleic Acids", *Bioelectrochemistry and Bioenergetics*, 20 (1988) pp 179–194.

* cited by examiner

CONTROL SYSTEM FOR ACTIVE PROGRAMMABLE ELECTRONIC MICROBIOLOGY SYSTEM

This is a continuation of application Ser. No. 08/304,657, filed on Sep. 9, 1994, now U.S. Pat. No. 5,632,957 issued on May 27, 1997, which is a continuation-in-part of Ser. No. 08/271,882, filed Jul. 7, 1994, now U.S. Pat. No. 6,017,696 issued on Jan. 25, 2000, which is a continuation-in-part of Ser. No. 08/146,504, filed Nov. 1, 1993, now issued as U.S. Pat. No. 5,605,662 on Feb. 27, 1997.

RELATED APPLICATION INFORMATION

This application is a continuation-in-part of application Ser. No. 08/271,882, filed Jul. 7, 1994, which is a continuation-in-part of Ser. No. 07/146,504, filed Nov. 1, 1993, both entitled "SELF-ADDRESSABLE SELF-ASSEMBLING MICROELECTRIC SYSTEMS AND DEVICES FOR MOLECULAR BIOLOGICAL ANALYSIS AND DIAGNOSTICS."

FIELD OF THE INVENTION

This invention relates to devices and systems for performing multi-step molecular biological type diagnostic analyses in multiplex formats. More particularly, the molecular biological type analyses include various nucleic acid hybridizations reactions and associated biopolymer synthesis. Additionally, antibody/antigen reactions and other clinical diagnostics can be performed.

BACKGROUND OF THE INVENTION

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual*, 2 Ed., Cold spring Harbor Laboratory Press, Cold Spring Harbor, N.Y. 1989).

Most of these techniques involve carrying out numerous operations (e.g., pipetting, centrifugations, electrophoresis) on a large number of samples. They are often complex and time consuming, and generally require a high degree of accuracy. Many a technique is limited in its application by a lack of sensitivity, specificity, or reproducibility. For example, these problems have limited many diagnostic applications of nucleic acid hybridization analysis. The complete process for carrying out a DNA hybridization analysis for a genetic or infectious disease is very involved. Broadly speaking, the complete process may be divided into a number of steps and substeps (see FIG. 1). In the case of genetic disease diagnosis, the first step involves obtaining the sample (blood or tissue). Depending on the type of sample, various pre-treatments would be carried out. The second step involves disrupting or lysing the cells, which then release the crude DNA material along with other cellular constituents. Generally, several sub-steps are necessary to remove cell debris and to purify further the crude DNA. At this point several options exist for further processing and analysis. One option involves denaturing the purified sample DNA and carrying out a direct hybridization analysis in one of many formats (dot blot, microbead, microtiter plate, etc.). A second option, called Southern blot hybridization, involves cleaving the DNA with restriction enzymes, separating the DNA fragments on an electrophoretic gel, blotting to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out the polymerase chain reaction (PCR) or other amplification procedure. The PCR procedure amplifies (increases) the number of target DNA sequences. Amplification of target DNA helps to overcome problems related to complexity and sensitivity in genomic DNA analysis. All these procedures are time consuming, relatively complicated, and add significantly to the cost of a diagnostic test. After these sample preparation and DNA processing steps, the actual hybridization reaction is performed. Finally, detection and data analysis convert the hybridization event into an analytical result.

The steps of sample preparation and processing have typically been performed separate and apart from the other main steps of hybridization and detection and analysis. Indeed, the various substeps comprising sample preparation and DNA processing have often been performed as a discrete operation separate and apart from the other substeps. Considering these substeps in more detail, samples have been obtained through any number of means, such as obtaining of full blood, tissue, or other biological fluid samples. In the case of blood, the sample is processed to remove red blood cells and retain the desired nucleated (white) cells. This process is usually carried out by density gradient centrifugation. Cell disruption or lysis is then carried out, preferably by the technique of sonication, freeze/thawing, or by addition of lysing reagents. Crude DNA is then separated from the cellular debris by a centrifugation step. Prior to hybridization, double-stranded DNA is denatured into single-stranded form. Denaturation of the double-stranded DNA has generally been performed by the techniques involving heating (>Tm), changing salt concentration, addition of base (NaOH), or denaturing reagents (urea, formamide, etc.). Workers have suggested denaturing DNA into its single-stranded form in an electrochemical cell. The theory is stated to be that there is electron transfer to the DNA at the interface of an electrode, which effectively weakens the double-stranded structure and results in separation of the strands. See, generally, Stanley, "DNA Denaturation by an Electric Potential", U.K. patent application 2,247,889 published Mar. 18, 1992.

Nucleic acid hybridization analysis generally involves the detection of a very small number of specific target nucleic acids (DNA or RNA) with an excess of probe DNA, among a relatively large amount of complex non-target nucleic acids. The substeps of DNA complexity reduction in sample preparation have been utilized to help detect low copy numbers (i.e. 10,000 to 100,000) of nucleic acid targets. DNA complexity is overcome to some degree by amplification of target nucleic acid sequences using polymerase chain reaction (PCR). (See, M. A. Innis et al, *PCR Protocols: A Guide to Methods and Applications*, Academic Press, 1990). While amplification results in an enormous number of target nucleic acid sequences that improves the subsequent direct probe hybridization step, amplification involves lengthy and cumbersome procedures that typically must be performed on a stand alone basis relative to the other substeps. Substantially complicated and relatively large equipment is required to perform the amplification step.

The actual hybridization reaction represents the most important and central step in the whole process. The hybridization step involves placing the prepared DNA sample in contact with a specific reporter probe, at a set of optimal conditions for hybridization to occur to the target DNA sequence. Hybridization may be performed in any one of a number of formats. For example, multiple sample nucleic acid hybridization analysis has been conducted on a variety of filter and solid support formats (See G. A. Beltz et al., in *Methods in Enzymology*, Vol. 100, Part B, R. Wu, L. Grossman, K. Moldave, Eds., Academic Press, New York, Chapter 19, pp. 266–308, 1985). One format, the so-called "dot blot" hybridization, involves the non-covalent attachment of target DNAs to filter, which are subsequently hybridized with a radioisotope labelled probe(s). "Dot blot" hybridization gained widespread use, and many versions were developed (see M. L. M. Anderson and B. D. Young, in *Nucleic Acid Hybridization—A Practical Approach*, B. D. Hames and S. J. Higgins, Eds., IRL Press, Washington, D.C. Chapter 4, pp. 73–111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757–758, 1992). These methods usually attach specific DNA sequences to very small specific areas of a solid support, such as microwells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Dramanac and R. Crkvenjakov, Yugoslav Patent Application #570/87, 1987; R. Dramanac et al., 4 Genomics, 114, 1989; Strezoska et al., 88 Proc. Natl. Acad. Sci. USA 10089, 1992; and R. Dramanac and R. B. Crkvenjakov, U.S. Pat. No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genomics 1008, 1992, proposed. using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Concurrently, Dramanac et al., 260 Science 1649–1652, 1993, used the second format to sequence several short (116 bp) DNA sequences. Target DNAs were attached to membrane supports ("dot blot" format). Each filter was sequentially hybridized with 272 labelled 10-mer and 11-mer oligonucleotides. A wide range of stringency condition was used to achieve specific hybridization for each n-mer probe; washing times varied from 5 minutes to overnight, and temperatures from 0° C. to 16° C. Most probes required 3 hours of washing at 16° C. The filters had to be exposed for 2 to 18 hours in order to detect hybridization signals. The overall false positive hybridization rate was 5% in spite of the simple target sequences, the reduced set of oligomer probes, and the use of the most stringent conditions available.

A variety of methods exist for detection and analysis of the hybridization events. Depending on the reporter group (fluorophore, enzyme, radioisotope, etc.) used to label the DNA probe, detection and analysis are carried out fluorometrically, calorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. A number of other factors also reduce the sensitivity and selectivity of DNA hybridization assays.

Attempts have been made to combine certain processing steps or substeps together. For example, various microrobotic systems have been proposed for preparing arrays of DNA probe on a support material. For example, Beattie et al., in *The 1992 San Diego Conference: Genetic Recognition*, Nov. 1992, used a microrobotic system to deposit micro-droplets containing specific DNA sequences into individual microfabricated sample wells on a glass substrate.

Generally, the prior art processes have been extremely labor and time intensive. For example, the PCR amplification process is time consuming and adds cost to the diagnostic assay. Multiple steps requiring human intervention either during the process or between processes is suboptimal in that there is a possibility of contamination and operator error. Further, the use of multiple machines or complicated robotic systems for performing the individual processes is often prohibitive except for the largest laboratories, both in terms of the expense and physical space requirements.

As is apparent from the preceding discussion, numerous attempts have been made to provide effective techniques to conduct multi-step, multiplex molecular biological reactions. However, for the reasons stated above, these techniques are "piece-meal" and limited. These various approaches are not easily combined to form a system which can carry out a complete DNA diagnostic assay. Despite the long-recognized need for such a system, no satisfactory solution has been proposed previously.

SUMMARY OF THE INVENTION

The present invention relates to the design, fabrication, and uses of a self-addressable self-assembling microelectronic devices and systems which can actively carry out controlled multi-step processing and multiplex reactions in a microscopic formats. These reactions include, but are not limited to, most molecular biological procedures, such as nucleic acid hybridization, antibody/antigen reaction, and related clinical diagnostics. In addition, the claimed devices and systems are able to carry out multi-step combinational biopolymer synthesis, including, but not limited to, the synthesis of different oligonucleotides or peptides at specific micro-locations on a given device.

The claimed devices and systems are fabricated using both microlithographic and micro-machining techniques. The basic device has a matrix of addressable microscopic locations on its surface; each individual micro-location is able to control electronically and direct the transport and attachment of specific binding entities (e.g., nucleic acids, enzymes, antibodies) to itself. All micro-locations can be addressed with their specific binding entities. The self-addressing process requires minimal outside intervention in terms of fluidics or mechanical components.

The device is able to control and actively carry out a variety of assays and reactions. Analytes or reactants can be transported by free field electrophoresis to any specific micro-location where the analytes or reactants are effectively concentrated and reacted with the specific binding entity at the micro-location. In the case of hybridization analysis, the sensitivity for detecting a specific analyte or reactant is improved because hybridization reactants are concentrated at a specific microscopic location. Any un-bound analyltes or reactants can be removed by reversing the polarity of a micro-location. Thus, the device also improves the specificity of the reactions. Basic devices for nucleic acid hybridization and other analyses are alternatively referred to as APEX devices, which stands for addressable programmable electronic matrix.

In one aspect of the invention, additional processing steps or substeps may be performed in sequence with a "system". The system is an integrated arrangement of component devices. Each component device is appropriately designed and scaled to carry out a particular function. In its most complete embodiment, a system may perform all aspects of sample preparation, hybridization and detection and analysis. In this fullest form, the sample is first prepared, such as by an electronic cell sorter component. Generally, electronic refers more specifically to the ability of the component device to electrophoretically transport charged entities to or from itself. Further DNA processing and complexity reduction may optionally be performed by a crude DNA selector component, and a restriction fragment selector component. The final processed target DNA is transported to the analytical component where electronic hybridization analysis is carried out in a microscopic multiplex format. This analytical component device is also referred to as the APEX or analytical chip. Associated detection and image analysis components provide the results.

Within the system materials may optionally be transported between components (devices) by free field electrophoresis, channelling, fluidics or other techniques. Optionally, electronic reagent dispenser components can provide electrophoretic transport of reagents to the various processing components of the system. Optionally, an electronic waste disposal system may be formed by providing an electrode and charged matrix material that attracts and holds charged waste products. Optionally, an electronic DNA fragment storage system can serve to temporarily hold other DNA fragments for later hybridization analysis.

In one aspect of this invention, genomic DNA complexity reduction is performed by processes that isolate those specific DNA fragments containing the desired target sequence from the bulk of the DNA material that lacks the desired target sequence. Crude DNA can be transported and captured on a support material. The bound DNA can then be severed using appropriate restriction enzymes. After severing, the DNA fragments can be transported to a component device that selectively hybridizes specific DNA fragments. Those fragments that contain the actual target sequences to be analyzed can be selectively released, via further restriction enzyme cleavage, and transported to the analytical component (APEX chip) of the system. Optionally, this procedure may be repeated for other fragments containing other target sequences.

A controller for the device (or system) provides for individual control of various aspects of the device. When an APEX device or chip containing addressable microscopic locations is utilized, the controller permits individual microlocations to be controlled electronically so as to direct the transport and attachment of specific binding entities to that location. The device may carry out multi-step and multiplex reactions with complete and precise electronic control, preferably under control of a microprocessor based component. The rate, specificity, and sensitivity of multi-step and multiplex reactions are greatly improved at the specific microlocations on the device. The controller interfaces with a user via input/output devices, such as a display and keyboard input. Preferably, a graphical user interface is adapted for ease of use. The input/output devices are connected to a controller, which in turn controls the electrical status of the addressable electronic locations on the system. Specifically, the controller directs a power supply/waveform generator to generate the electronic status of the various microlocations. Optionally, an interface is used between the power supply/waveform generator and the APEX device or system. The interface preferably comprises a bank of relays subject to the controller via a multifunction input/output connection. The relays preferably serve to connect the power supply/waveform generator to the APEX device by controlling the connection as to its polarity, the presence or absence of a connection and the amount of potential or current supply to the individual location. The controller preferably controls the illumination source directed at the hybridization system. A detector, image processing and data analysis system are optically coupled to the APEX device. In the preferred embodiment, a fluorescent microscope receives and magnifies the image from the hybridization events occurring on the various micro-locations of the device.

The emissions are optically filtered and detected by a charge coupled device (CCD) array or microchannel plate detector. The image is then stored and analyzed. Preferably, the results are displayed to the user on the monitor.

In another aspect of this invention, the hybridization system is formed having a plurality of microlocati ons formed atop a substrate containing control electronics. Specifically, switching circuits are provided to address individually the microlocations. The electrical connections are made via the backside relative to where sample contact is to be made. Additionally, an optical pathway, such as a waveguide, is disposed beneath the microlocation to permit backside access to the microlocation. Optical excitation, if necessary, may be directed to the microlocation via the waveguide. Detection of emitted radiation may be detected via the backside waveguide. In yet another aspect of this invention, a sample containment system is disposed over the system, particularly the hybridization matrix region. In the preferred embodiment, the matrix hybridization region (including sample containment component) is adapted for removal from the remainder of the device providing the electronic control and detector elements.

In another aspect of this invention, improved processes for forming a matrix hybridization system are described. In one process, a substrate, such as silicon, is formed with an insulating layer, such as a thick oxide. Conductive microlocations are formed, such as by deposition of metal (e.g., aluminum or gold) that is then patterned, such as by conventional photolithographic techniques. An insulating coating is formed, such as TEOS formed by PECVD. Optionally, a nitride passivation coating is formed over the TEOS layer. Openings to the microelectrode are formed through the nitride and glass. Optionally, adhesion improving materials such as titanium tungsten may be utilized in connection with the metal layer to promote adhesion to the oxide and/or glass. In yet a further improvement, wells may be formed atop of the electrode by undercutting a nitride layer disposed on an oxide layer supported by the substrate.

Electronic control of the individual microlocations may be done so as to control the voltage or the current. When one aspect is set, the other may be monitored. For example, when voltage is set, the current may be monitored. The voltage and/or current may be applied in a direct current mode, or may vary with time. For example, pulsed currents or DC biases may be advantageously utilized.

Accordingly, it is an object of this invention to provide a system for the sample preparation, processing, hybridization, detection and analysis of biological materials.

It is yet a further object of this invention to provide a system that combines multiple steps or substeps within an integrated system.

It is yet a further object of this invention to provide for an automated DNA diagnostic system.

DETAILED DESCRIPTION OF THE INVENTION

Figure 1:
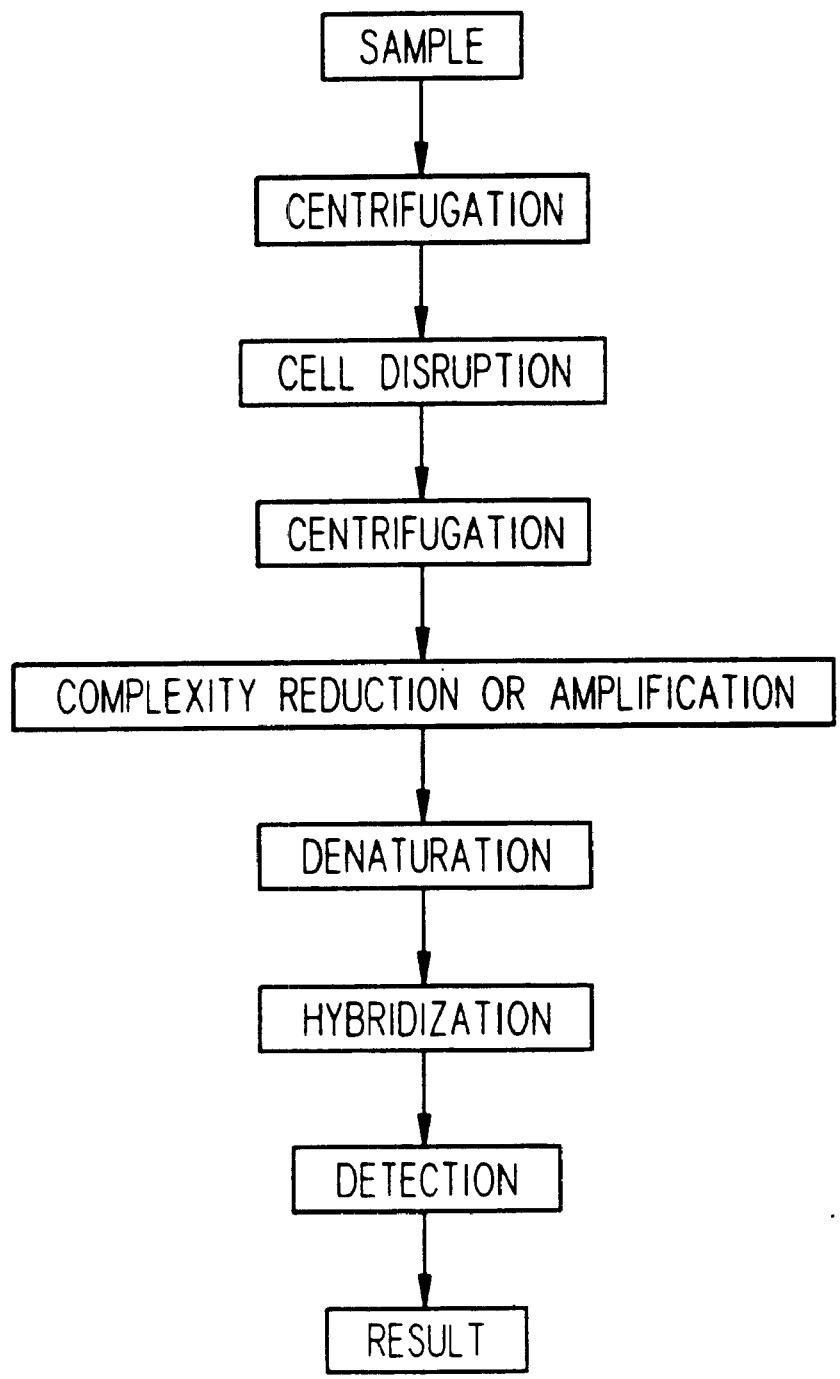
FIG. 1 shows the sequence of steps and substeps for sample preparation, hybridization and detection and data analysis.
Figure 2A:
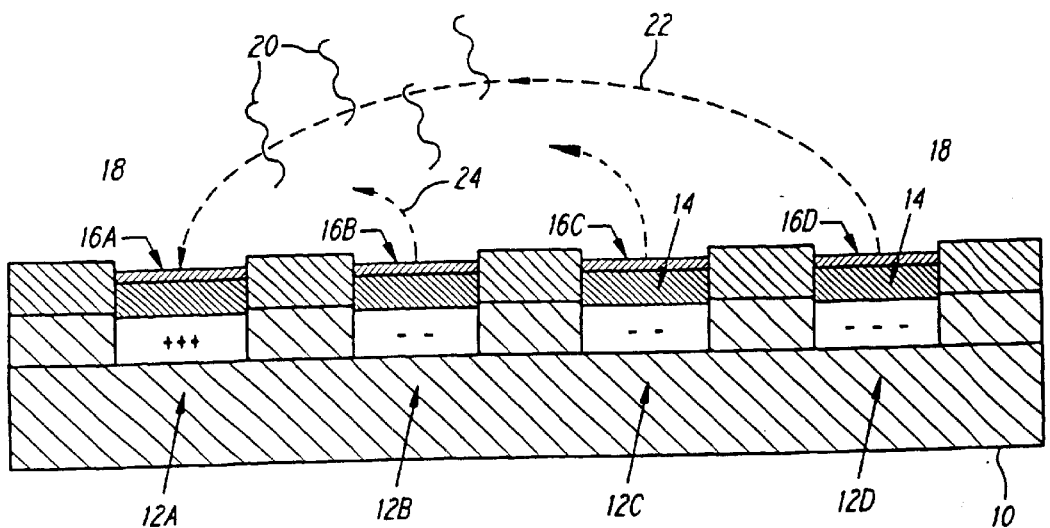
FIGS. 2A and 2B show the active, programmable matrix system in cross-section (FIG. 2A) and in perspective view (FIG. 2B).
Figure 2B:
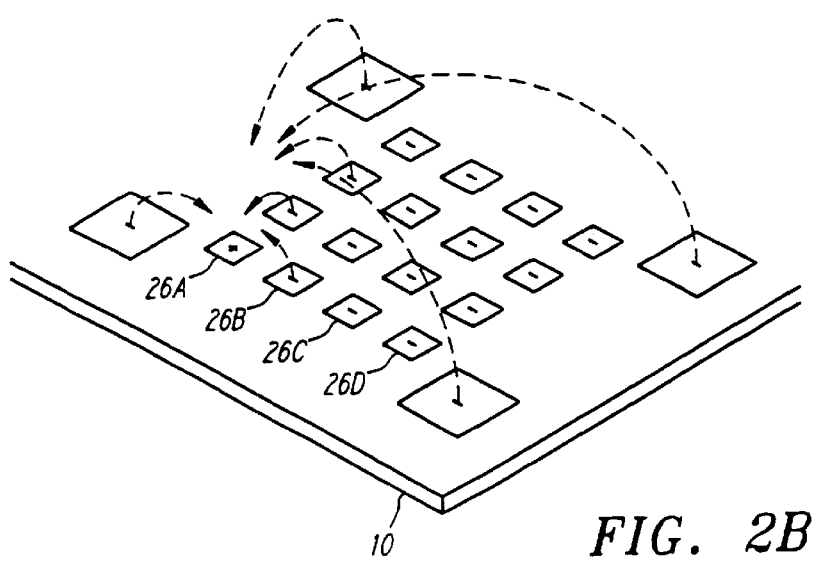

FIGS. 2A and 2B illustrate a simplified version of the active programmable electronic matrix hybridization system for use with this invention. Generally, a substrate supports a matrix or array of electronically addressable microlocations 12. For ease of explanation, the various microlocations in FIG. 2A have been labelled 12A, 12B, 12C and 12D. A permeation layer 14 is disposed above the individual electrodes 12. The permeation layer permits transport of relatively small charged entities through it, but precludes large charged entities, such as DNA, from contacting the electrodes 12 directly. The permeation layer 14 avoids the electrochemical degradation which would occur in the DNA by direct contact with the electrodes 12. It further serves to avoid the strong, non-specific adsorption of DNA to electrodes. Attachment regions 16 are disposed upon the permeation layer 14 and provide for specific binding sites for target materials. The attachment regions 16 have been labelled 16A, 16B, 16C and 16D to correspond with the identification of the electrodes 12A–D, respectively.

In operation, reservoir 18 comprises that space above the attachment regions 16 that contains the desired, as well as undesired, materials for detection, analysis or use. Charged entities 20, such as charged DNA are located within the reservoir 18. In one aspect of this invention, the active, programmable, matrix system comprises a method for transporting the charged material 20 to any of the specific microlocations 12. When activated, a microlocation 12 generates the free field electrophoretic transport of any charged functionalized specific binding entity 20 towards the electrode 12. For example, if the electrode 12A were made positive and the electrode 12D negative, electrophoretic lines of force 22 would run between the electrodes 12A and 12D. The lines of electrophoretic force 22 cause transport of charged binding entities 20 that have a net negative charge toward the positive electrode 12A. Charged materials 20 having a net positive charge move under the electrophoretic force toward the negatively charged electrode 12D. When the net negatively charged binding entity 20 that has been functionalized contacts the attachment layer 16A as a result of its movement under the electrophoretic force, the functionalized specific binding entity 20 becomes covalently attached to the attachment layer 16A.

It is possible to protect the attachment layers which are not subject to reaction, such as 16B and 16C by making their corresponding electrodes 12B and 12C negative. This results in electrophoretic lines of force emanating from the attachment region 16B (only 16B will be discussed for simplicity, the results being similar for 16C). The electrophoretic force lines 24 serve to drive away negatively charged binding entities from the attachment layer 16B and towards the attachment layer 16A. In this way, a "force field" protection is formed around the attachment layers 16 which it is desired to have nonreactive with the charged molecules at that time.

One highly advantageous result of this system is that charged binding materials 20 may be highly concentrated in regions adjacent to signal attachment layers 16. As can be seen in perspective drawing FIG. 2B, if a individual microlocation 26A is positively charged, and the remaining microlocation are negatively charged, the lines of electrophoretic force will cause transport of the net negatively charged binding entities 20 toward the microlocation 26A.

The microlocation 26A is intended to depict the combination in FIG. 2A of the attachment layer 16, the permeation layer 14 and the underlying associated electrode 12. In this way, a method for concentrating and reacting analytes or reactants at any specific microlocation on the device may be achieved. After the attachment of the specific binding entities 20 to the attachment layer 16, the underlying microelectrode 12 may continue to function in a direct current (DC) mode. This unique feature allows relatively dilute charged analytes or reactant molecules free in solution to be rapidly transported, concentrated, and reacted in a serial or parallel manner at any specific micro-location that is maintained at the opposite charge to the analyte or reactant molecules. This ability to concentrate dilute analyte or reactant molecules at selected microlocations 26 greatly accelerates the reaction rates at these microlocations 26.

After the desired reaction is complete, the electrode 12 may have its potential reversed thereby creating an electrophoretic force in the direction opposite to the prior attractive force. In this way, nonspecific analytes or unreacted molecules may be removed from the microlocation 26. Specific analytes or reaction products may be released from any microlocation 26 and transported to other locations for further analysis; or stored at other addressable locations; or removed completely from the system. This removal or deconcentration of materials by reversal of the field enhances the discrimination ability of the system by resulting in removal of nonspecifically bound materials. By controlling the amount of now repulsive electrophoretic force to nonspecifically bound materials on the attachment layer 16, electronic stringency control may be achieved. By raising the electric potential at the electrode 12 so as to create a field sufficient to remove partially hybridized DNA sequences, thereby permitting identification of single mismatched hybridizations, point mutations may be identified.

Operations may be conducted in parallel or in series at the various attachment layers 16. For example, with reference to FIG. 2A, a reaction may occur first at attachment layer 16A utilizing the potentials as shown. The potential at electrode 12A may be reversed, that is, made negative, and the potential at the adjacent electrode 12B may be made positive. In this way, a series reactions occurs. Materials that were not specifically bound to attachment layer 16A would be transported by electrophoretic force to attachment layer 16B. In this way, the concentration aspect is utilized to provide high concentrations at that specific attachment layer then subject to the positive electrophoretic force. The concentrated materials may next be moved to an adjacent, or other, attachment layer 16. Alternatively, multiple attachment layers 16 may be deprotected in the sense that there is a net electrophoretic force field emanating from the electrode 12 through the attachment layer 16 out into the reservoir 18. By deprotecting multiple attachment layer 16, multiplex reactions are performed. Each individual site 26 may serve in essence as a separate biological "test tube" in that the particular environment addressed by a given attachment layer 16 may differ from those environments surrounding the other attachment layers 16.

Figure 3:
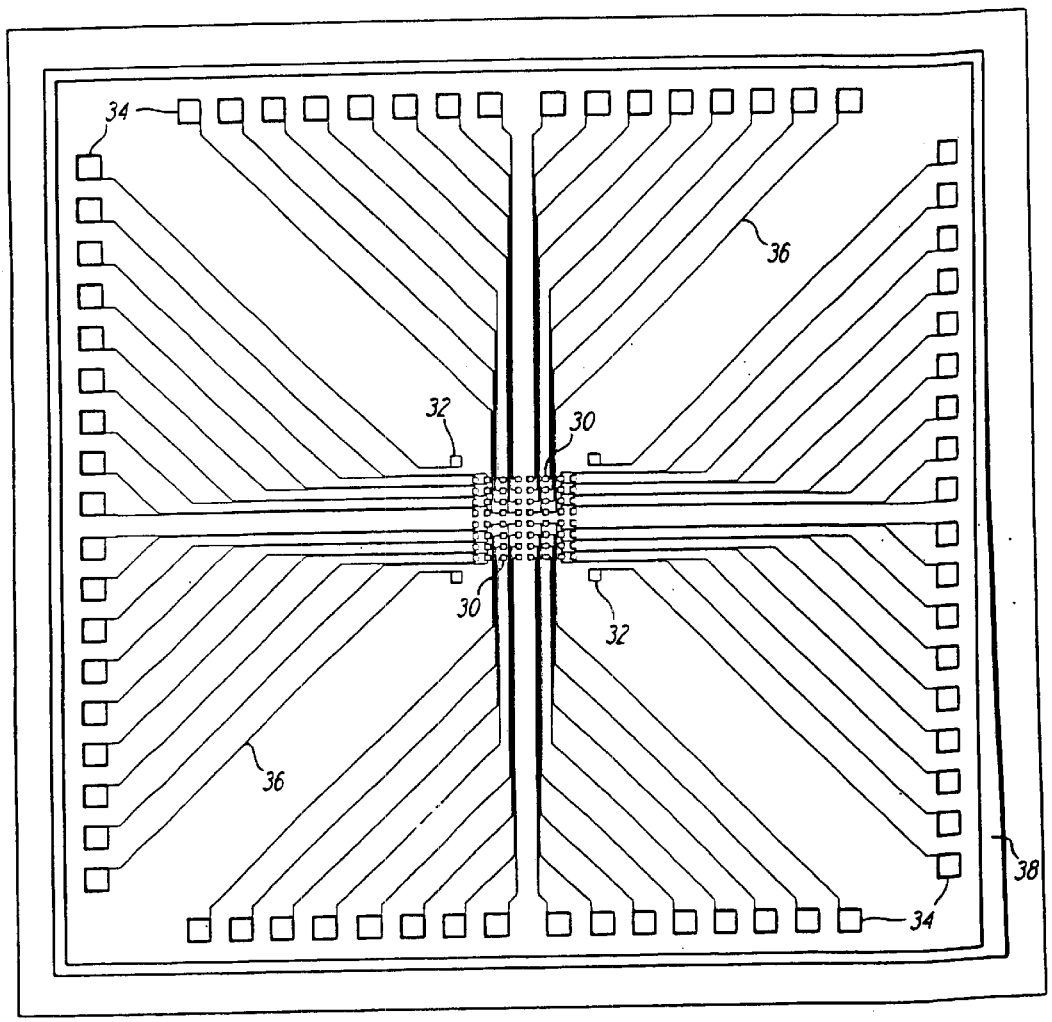
FIG. 3 shows the active, programmable matrix system structure at the metal mask layer.

FIG. 3 shows a plan view of the metal mask layer for an active programmable electronic matrix system. A plurality of individual electrodes 30 are formed preferably in an array. For example, an 8×8 matrix of individual electrodes 30 is formed. Optionally, additional control or dump pads 32 may be provided to aid in generation of desired electrophoretic fields. The electrodes 30 and pad 32 are connected to contact pads 34. 68 contact pads 34 are shown corresponding to the 64 electrodes 30 and 4 pads 32. Leads 36 connect the electrodes 30 and pads 32 individually to the contacts 34. As shown, a fan-out pattern is used to permit connections from the relatively condensed region of the electrodes and pads 32 to the boundaries 36 of the mask.

Figure 4:
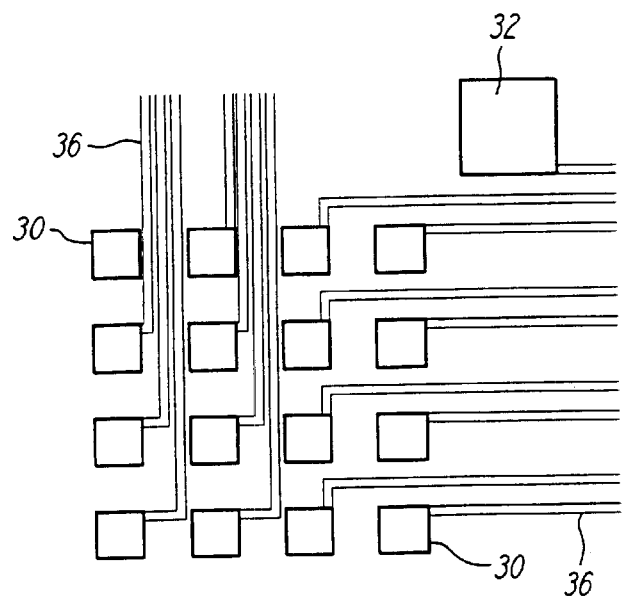
FIG. 4 shows detail of the active, programmable matrix system in plan view.

FIG. 4 shows an exploded detail plan view of the mask of FIG. 3. The resulting metallized system would appear substantially similar to the masked pattern. The electrodes 30 are shown formed as substantially square structures. The lead lines 36 connect the electrode 30 to the contact pad 34 (FIG. 3). The preferred line width of the lead 36 is 1 to 20 microns.

Figure 5:
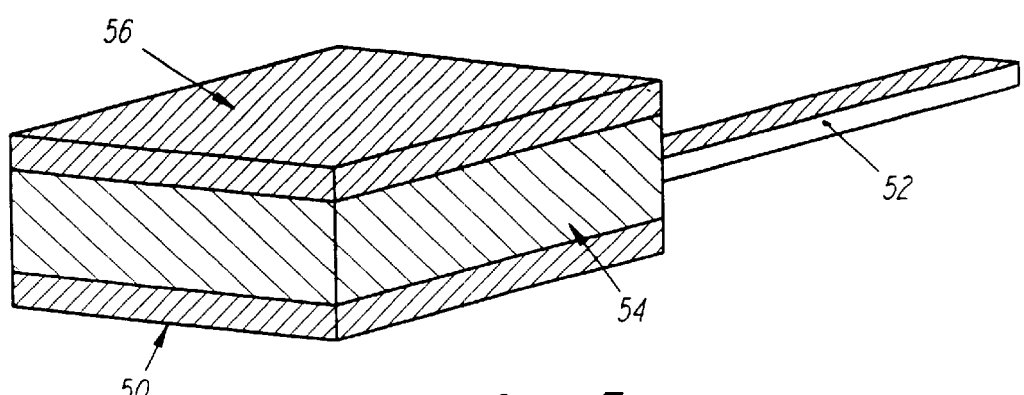
FIG. 5 shows a perspective view of a single microlocation and electrical connection.

FIG. 5 shows a perspective view of a single electrode 50. The electrode 50 is connected directly to the lead 52. A permeation layer 54 is disposed above the lead 50. An attachment layer 56 is disposed upon the permeation layer 54.

The permeation layer in microlithographically produced devices can range in thickness from 1 nm to 500 micrometers, with 500 nm to 50 micrometers being the most preferred. The permeation layer should cover the entire electrode surface. The permeation layer may be formed from any suitable material such as polymers, ceramics, sol-gels, layered composite materials, clays and controlled porousity glass.

Figure 6:
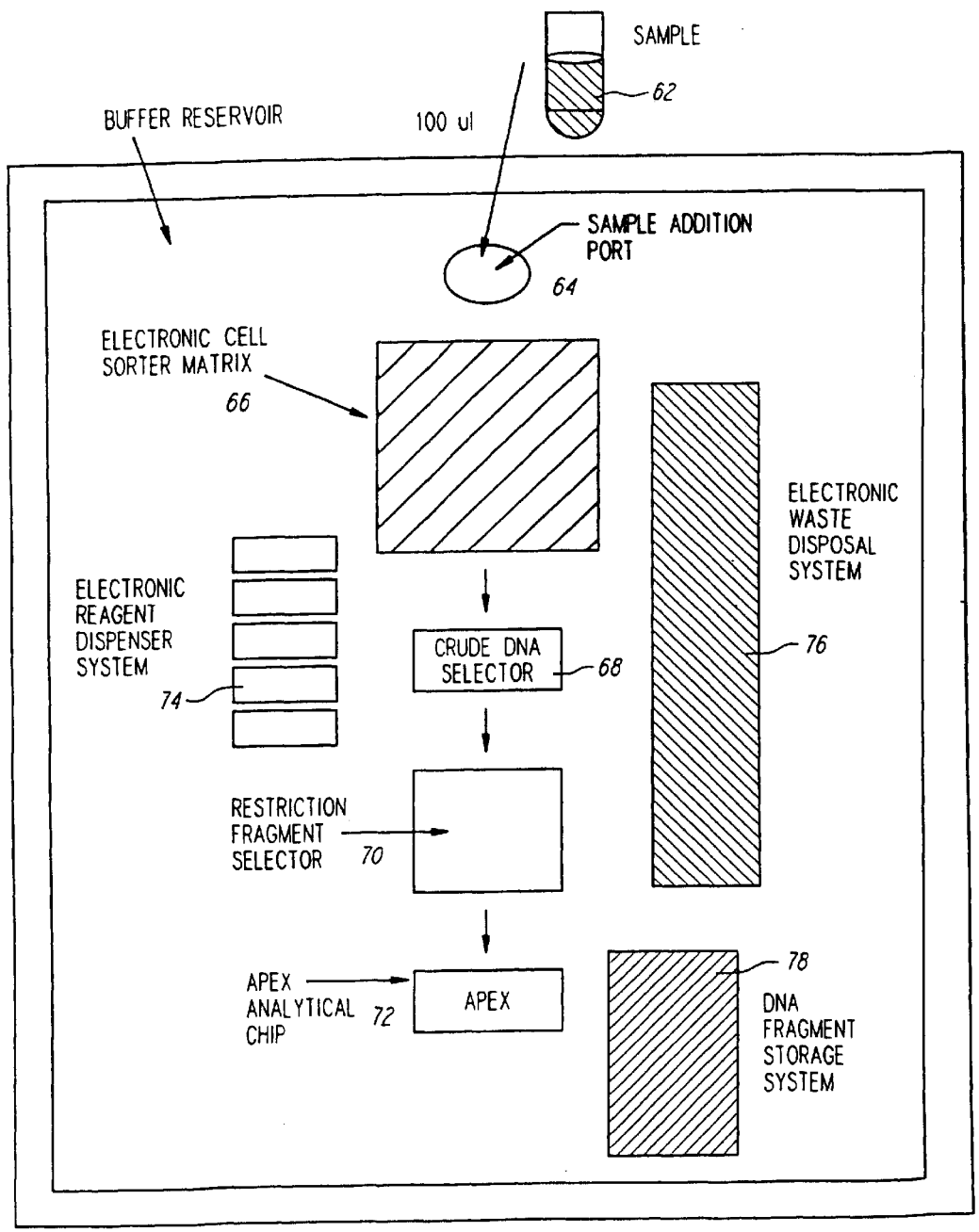
FIG. 6 shows a plan view of the system including an electronic cell sorter matrix, DNA selectors and restriction fragment selectors and hybridization matrix.

FIG. 6 shows a complete system 60 for the automated sample preparation and hybridization of prepared materials. A sample 62, such as blood or other biological materials are introduced into the system 60. Generally, a sample addition port 64 is provided. Generally, the sample addition port 64 is utilized when an overlying biological containment structure is present such that the sample 62 could not be directly placed into the system without access via the port 64.

Sample preparation is performed in this system 60 by the combination of the electronic cell sorter matrix component 66 and DNA selector component 68 and restriction fragment selector component 70. The electronic cell sorter matrix component 66 consists of underlying electrodes, with permeation layers and an attachment layers. These effectively form a matrix of locations for the attachment of cells. Generally, the area for individual locations and the complete matrix area are larger than the areas in an analytical device component. Thus, the electronic cell sorter matrix is scaled appropriately to accommodate variation in the number of cells from different samples and sample sizes. The attachment layers can be generally selective for cells, or individual selective for different types of cells. Optionally, groups or sets of locations can be made selective for one type of cell. Cell selectivity can be imparted by attaching specific antibodies or cell adhesion factors to the attachment layer. The matrix 66 operates by free field electrophoresis.

The crude DNA selector 68 and restriction fragment selector 70 serve to bind the crude DNA output from the electronic cell sorter matrix 66 and permit selective cleavage of the desired DNA from the bound material. The term crude is used merely to denote a non-final stage in DNA isolation or complexity reduction. The DNA is bound to the selector in a region which is believed not to contain the desired DNA material. The desired DNA materials are then severed from the bound materials, such as by application of restriction enzymes. The severed, unbound material is then physically moved from the crude DNA selector 68 to the restriction fragment selector 70. Preferably, electrophoretic transport is used to remove the severed material. This process may be repeated by binding the severed material to a selector, upon which a restriction enzyme acts so as to cleave the unbound portion which contains the desired DNA.

For example, human DNA contains approximately 100,000 genes. Of the total DNA material, a significant portion constitutes repeating sequences which do not contain the desired DNA information. The DNA may be bound to a selector by these noninformation bearing repeating sequences. The bound DNA may be severed from the unbound DNA which is believed to contain the desired DNA to be analyzed. This process may then be repeated with yet more specific sequences causing binding of the material to the selector.

The output of the restriction fragment selector 70 is then supplied to the APEX chip 72. Operations on the matrix 72 are performed as described in connection with FIGS. 2A and 2B.

An alternative technique for reducing DNA complexity is to use DNA-based affinity chromatography. The affinity that a piece of single stranded DNA has for another single stranded piece of DNA depends on how closely the base pairs match. When the stationary phase of a chromatographic system contains a particular sequence or collection of sequences,. any single stranded DNA in the mobile phase will adhere to the stationary phase more or less well depending on how closely the sequence matches the capture sequence/s in the stationary phase. This allows chromatographic separations based on the affinity of DNA for capture sequences in the stationary phase.

One method to implement DNA-based affinity chromatography with a matrix of micro-locations is to modify a series of locations with capture probe of a particular sequence or set of sequences. This forms the stationary phase. A sample of DNA is addressed to a microlocation and is moved serially from one micro-location to the next. Electronic stringency control is used to retain the DNA that matches the capture probe well at each micro-location. In this way, DNA that matches the capture probe will be removed rapidly from the sample.

Figure 16:
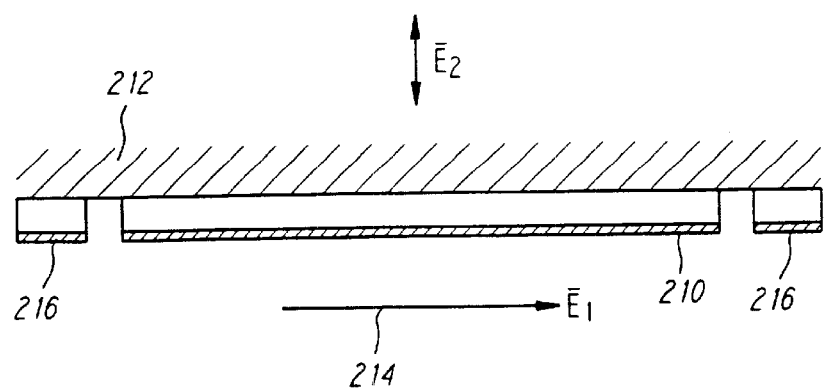
FIG. 16 shows a cross-sectional view of a DNA purification system.

The invention of serial purification of a DNA sample by DNA-based affinity chromatography on a series of micro-locations can be generalized to a continuous version. FIG. 16 shows a cross-sectional view of such a system. Here, the electrode 210 forms a long strip and is modified by an appropriate stationary phase. The mobile phase is confined to a channel 212 above the stationary phase. The mobile phase can be passed over the stationary phase by convective mass transport. Alternatively, ions in the mobile phase can be pulled along the stationary phase by an electric field 214 established by placing separate and independent electrodes 216 at either end of the long strip electrode. Electronic stringency can be used by applying an alternating or pulsed current at the strip electrode. This drives DNA on and off of the stationary phase.

A further alternative method for reducing the complexity of a sample of DNA, is to size select by sieving the sample through a microporous media. Microporous media can be formed by filling cavities of arbitrary geometry with dendrites. These dendrites are formed by electrochemical deposition of chemicals such as, but not exclusive to, metal salts, ceramic forming materials, monomers and polymers. The porosity of the microporous media can be controlled by adjusting the electrical signal that is applied to the electrodes. For example, dendrites can form picket fence type structures or fractal type structures.

A method for forming microporous media on an APEX device could involve forming a long channel with opposing metal electrodes. When this channel is filled with the appropriate chemical and an appropriate electrical signal is applied to the electrodes, dendrites will form in the-interstitial space between the electrodes forming a microporous media.

Returning to FIG. 6, an electronic reagent dispenser system 74 may be provided to deliver reagents to the system 60. Preferably, the reagents are delivered by electrophoretic force. if they are charged. Optionally, an electronic waste disposal system 76 is included within the system 60. The waste disposal system 76 attracts charged waste particles to it and disposes of them by holding the charged entities on it. Another optional member of system 60 is the DNA fragment storage system 78. This fragment storage system 78 serves to temporarilly hold DNA fragments for future analysis.

The system 60 may include some or all of the functions described above. For example, the combination of sample preparation in the form of complexity reduction, as performed by the DNA selector 68 and restriction fragment selector 70 may be associated with the analytical matrix 72. However, any or all of the above described functions may be combined as desired.

Figure 7:
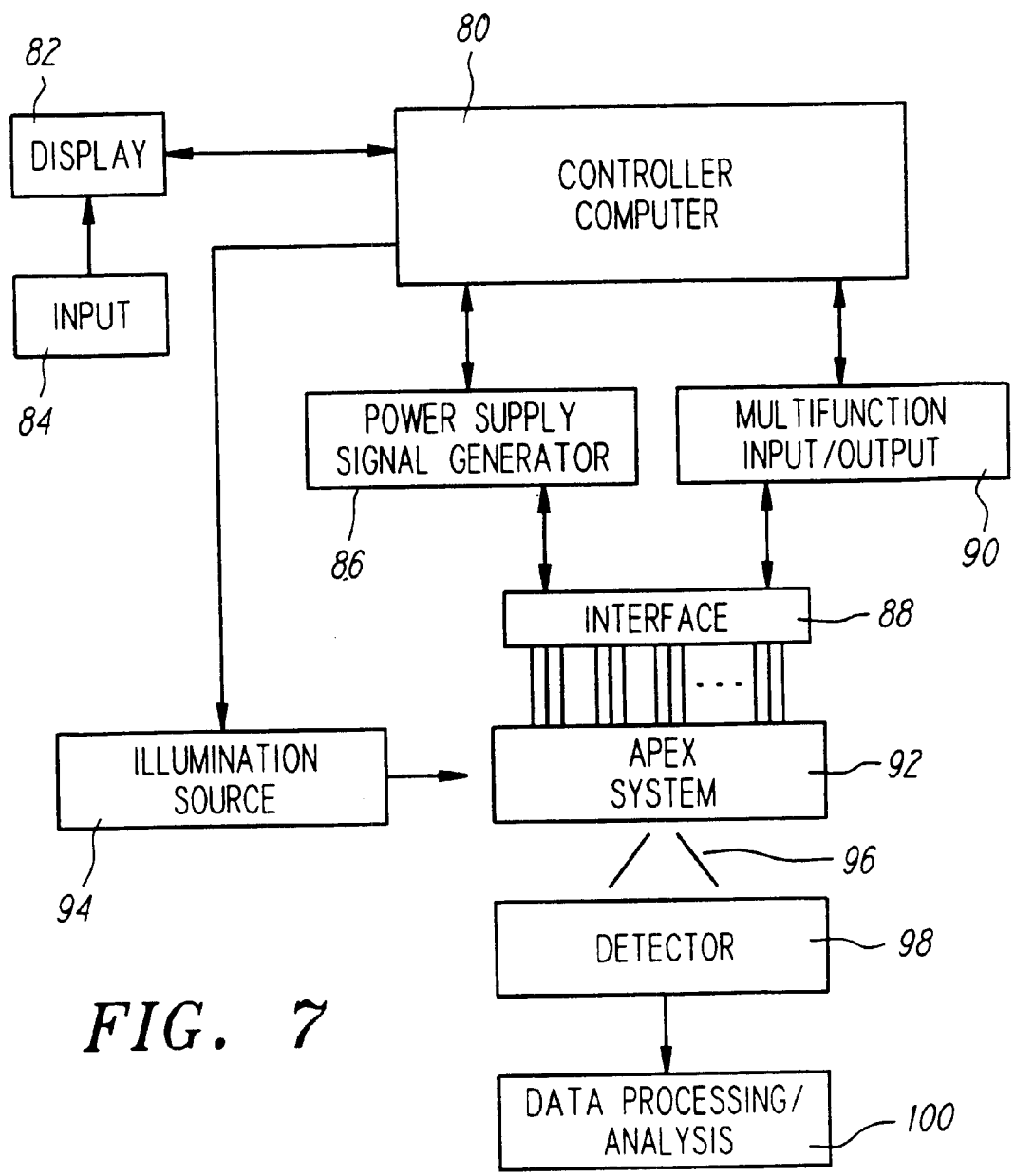
FIG. 7 shows a block diagram description of the control system.

FIG. 7 shows a block diagram of the overall system including the controller. The underlying electrodes in an APEX device are made active by the application of a controlled potential to the electrode or by the sourcing of a controlled current through the electrode. Full functionality is realized when the potential or current at each electrode of the APEX device is independently controlled. This is accomplished by an APEX controller system.

The controller computer 80 interfaces with user input/output devices, such as a display 82 and input device 84. The display 82 may be any form of conventional display such as a monitor or computer screen. The input 84 may be any conventional user input device, such as a keyboard, mouse, or touch-screen device. The controller computer 80 is connected with the power supply and waveform generator 86. The controller 80 sets the power supply and waveform generator 86 to provide the current or voltage output to the interface 88. In the preferred embodiment, the power supply or waveform generator 86 is capable of providing precisely regulated and voltage and current sourcing. The controller computer 80 provides control signals to the interface 88 via the multifunction input/output board 90. The interface 88 provides a simplified connection to the contacts for the APEX system 92.

The interface preferably includes relays that permit selective connection between the power supply and waveform generator 86 to the specific electrodes of the APEX system 92. In one embodiment, the interface 88 comprises a plurality of relays which connect the power supply and waveform generator 86 to the APEX system 92 electrodes. The connections permit the selection or non-selection of a path between the power supply and waveform generator 86 to the APEX system 92 electrodes. Additionally, another relay permits selecting the polarity of the voltages supplied to the APEX system 92 elec trodes. Optionally, if multiple source levels are available, such as from a multiple output power supply 86, the specific level to be connected to an APEX system 92 electrode may be set independently of those for the other electrodes.

Thus, as described in connection with FIG. 2A, by placing certain electrodes (e.g., 12B and 12C) at a negative, but lesser potential than electrode 12D, the attachment region 16B and 16C would be protected by the local force field.

The interface 88 may serve to select the desired voltage for the individual electrodes in the APEX system 92. Alternatively, such a different voltage arrangement may be achieved through use of a voltage divider.

In the preferred embodiment, the controller computer 80 is a Macintosh Quadra 950. National Instruments Corporation LabVIEW software is used to provide a software interface for a user to program the devices connected to the APEX and to collect and process data from an assay. National Instruments NuBus boards are used to provide the hardware interface from the Quadra 950 computer 80 to the power supply devices 86 that source potentials and currents and that measure the actual currents and potentials and the results of the assay. The user controls the assay through a Virtual Instrument created with the LabVIEW software. The virtual instrument provides a user friendly graphical representation of the controls that the user may exercise, and of some of the results of applying these controls to the APEX device to perform an assay. The user interfaces with the Virtual Instrument through the keyboard and mouse (collectively, input 84) of the Quadra 950 computer 80. The Virtual Instrument provides software interfaces to a National Instruments NB-MIO-16XL multipurpose input/output 90 and to a National. Instruments DMA2800 board that are connected to the NuBus data bus of the Quadra 950.

The multipurpose I/O board is able to provide digital and/or analog signals to external devices to implement the programmed sequence specified by the user through the Virtual Instrument. The MIO board is also able to digitize and store in the Quadra 950, under control of the Virtual Instrument, signals generated by the devices connected to the APEX. The DMA2800 provides the ability to store rapidly the data acquired by the MIO board through Direct Memory Access, bypassing the Quadra 950 CPU. The DMA 2800 also provides a GPIB (IEEE 488) interface for control of external devices that adhere to the IEEE 488 communication and data transfer standard, which includes most modern instruments.

In this preferred embodiment of the controller, two external devices are used to source the potentials or currents to the APEX. A Keithley 236 Source/Measure Unit power supply 86 provides adequate stability and flexibility as a source of precisely regulated potential or current. The SMU 236 either applies a potential and measures the resultant current or provides a source of current and measures the resultant potential. This device is programmed from the Virtual Instrument under GPIB control through the DMA2800 board to control the current or potential levels and time dependence, and to measure and store the actual potentials and currents that are sourced to the APEX.

The sourced currents or potentials are applied to the APEX through an array of relays in interference 88 that provide independent switching of each electrode between no connection, connection to positive source and connection to negative source. The preferred embodiment also provides for more than one Source/Measure supply to be utilized to provide different levels of positive and negative potential or current to different electrodes. The array of relays is provided by a National Instruments SCXI Chassis with nine 16-channel, Class 3 Relay Modules connected in the chassis, providing a total of 144 relays. Two relays are used per electrode to provide for electrode disconnected or electrode connected to either positive or negative source. In the preferred embodiment, a bundle of cables connects these relays to the APEX device through a Cerprobe Probe Card that provides mechanical contact of probes to the bond pads of the APEX device.

The controller computer 80 optionally controls the illumination source 94 for excitation of fluorescence to detect DNA hybridization. In the preferred embodiment, the illumination source 94 is a laser which outputs radiation at an appropriate wavelength to excite fluorescent markers included within the APEX system 92.

The output of the APEX system 92 is passed through observation path 96 to the detector 98. The observation path 96 may be a physical connection, such as through a fiber optic, or may comprise an optical path such as through a microscope. Optical filters may be utilized in the observation path to reduce illumination of the detector at wavelengths not corresponding to the emission spectra of the fluorescent markers in the APEX system 92. Additionally, notch filters may be utilized as necessary to reduce illumination of the detector 98 at the excitation wavelength of the laser illumination source 94. The detector 98 may optionally form an image of the APEX system 92, such as through the use of a cooled CCD camera. In addition to, or as an alterative to, forming an optical image, the emitted fluorescence radiation from the APEX system 92 may be detected by conventional means such as photodiodes or photomultiplier tubes. The output of the detector 98 is provided to the data processing/analysis system 100. This system monitors the level of detected probe material in the APEX system 92. Optionally, an expert system may be utilized in the analysis system 100.

In the preferred embodiment, a Data Translation Frame Grabber board is interfaced to the Quadra 950 NuBus, to provide capture to memory of images recorded by video cameras such as the Optronics cooled color CCD camera used in the preferred embodiment. This CCD camera observes the APEX device through a microscope with appropriate filters to provide visualization of fluorescence on the APEX array.

Figure 8:
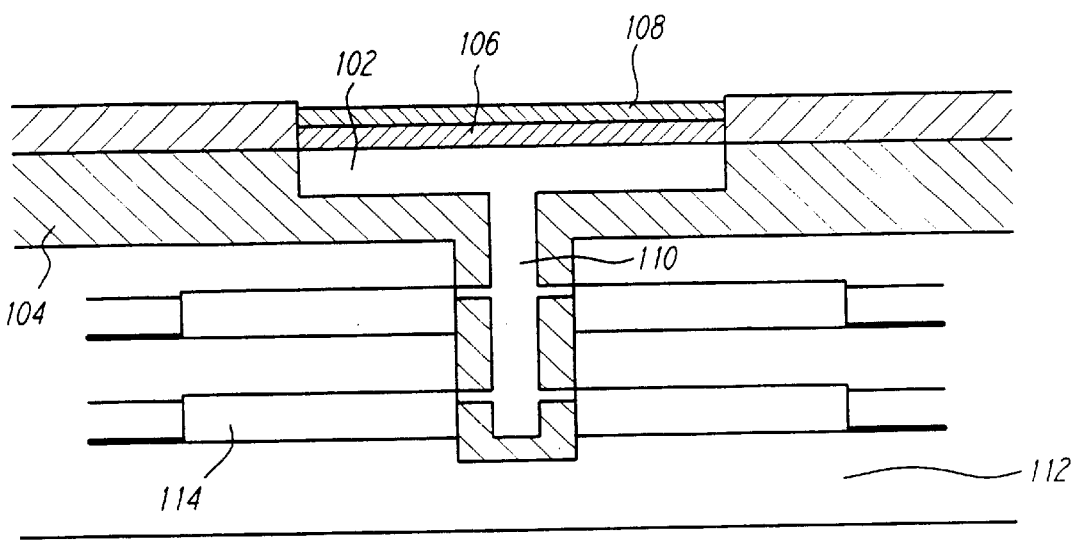
FIG. 8 is a cross-sectional view of the active, programmable matrix system having associated electronics.

Alternate systems may implement all the functionality of the controller as described, but may use custom devices incorporated into printed circuit boards and custom software to control the board with a similar user-friendly interface for programming the device. These alternate systems may also incorporate the switching elements of the array of relays into a semiconductor device underlying the active, programmable matrix system. FIG. 8 shows a cross-sectional view of an alternative embodiment for the active, programmable matrix system. Individually addressable electrodes 102 are formed upon a support layer 104. Preferably, the support layer 104 is an insulator. Above the electrodes 102 is preferably disposed permeation layer 106 and individual attachment layers 108 corresponding to the individual electrodes 102. Electrical connections 110 are provided from the backside of the electrodes 102 through the support 104. Additionally, a semiconductor support 112 includes circuit elements 114 connected to the conductor 110. The circuit elements 114 may be formed on or in the semiconductor 112. The circuit elements 114 may provide individual control of the voltage and or current provided via the conductor 110 to the electrode 102. In particular, the circuit elements 114 may incorporate the switching elements of the array of relays described in the preferred embodiment. Multiple current/voltage source lines 116 to each circuit element 114 provide the capability to source different levels to different electrodes 102. Memory type address lines 118 provide convenient activation paths for the individual circuit elements 114.

Waveguides can be used for guiding excitation light to micro-locations, and for guiding fluorescence signals to detectors. Waveguides can be free standing, as in an optical fiber, or can be integrated into a monolithic semiconductor device. Waveguides can be fabricated from materials such as zinc oxide or indium tin oxide that are also electrically conductive. The waveguide can then serve as both an electrode and as means for transporting optical radiation.

Waveguides can be located in or around the plane of the capture probe to minimize nonspecific background fluorescence. Waveguides can incorporate holographic optical elements. The function of these holographic optical elements includes, but is not exclusive to, notch filters, dichroic mirrors, band pass filters, beam splitters, neutral density filters, half-wave plates, quarter-wave plates, polarizers, and lenses.

Figure 9:
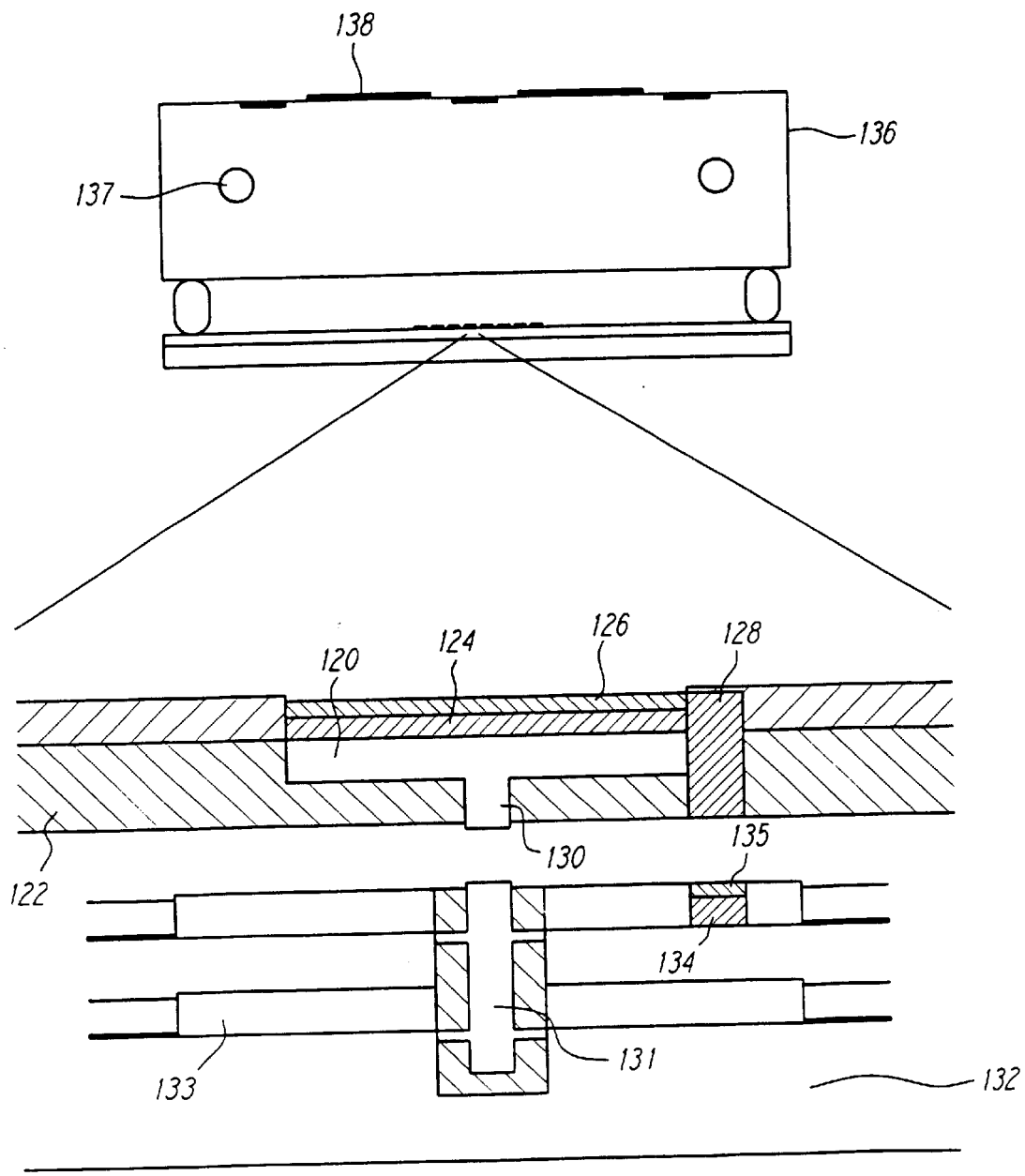
FIG. 9 is a cross-sectional view of an alternative, layered active, programmable matrix system having electrical and optical access to the backside of the microlocations and a biological containment cover.

FIG. 9 shows in cross-section an alternative, layered structure for the. active programmable matrix system. In a first layer, individual electrodes 120 are formed upon a support 122. The support 122 is preferably insulating. Above the electrodes 120 is preferably formed a permeation layer 124 and individual attachment layers 126 corresponding to the individual electrodes 120. Optical paths 128 are provided through the support 122 to access the electrode 120. Preferably, the optical path 128 is comprised of a fiber optic or light guiding pipe or structure. Optionally, electrical connection 130 passes through the support 122 to access the electrodes 120 from the backside. The term backside is used herein to connote that side of the electrode 120 which contacts the support 122. In a second layer a semiconductor support 132 includes circuit elements 133 connected to the conductor 131. The conductor 131 is designed such that its upper surface mates and forms good electrical contact with the bottom of the conductor 130 on the backside of the first layer. The circuit elements 133 may be formed on or in the semiconductor 132. The circuit elements 133 may provide individual control of the voltage and or current provided via the mated conductors 131 and 130 to the electrode 120. In particular, the circuit elements 133 may incorporate the switching elements of the array of relays described in the preferred embodiment. These circuit elements may be supplied by multiple current/voltage source lines and may be activated by memory type address lines. Optionally, detector elements 134, such as photodiodes may be incorporated in the semiconductor layer 132 and coupled through optical paths 135 with the optical paths 128 of the first layer, so that the detector elements monitor DNA hybridization at the attachment sites 126 of the first layer. These optical paths can implemented as fiber optic paths or as waveguides and can incorporate various optical elements as described above. Optionally, a sample containment vessel 136 may be disposed around the structure to contain the biological material under analysis or test. Optionally, fluid input ports 137 or optical viewing ports 138 may be provided. The biological containment structure 136 and optional port 137 and 138 may be used in connection with any of the active, programmable matrix systems described herein.

Figure 10:
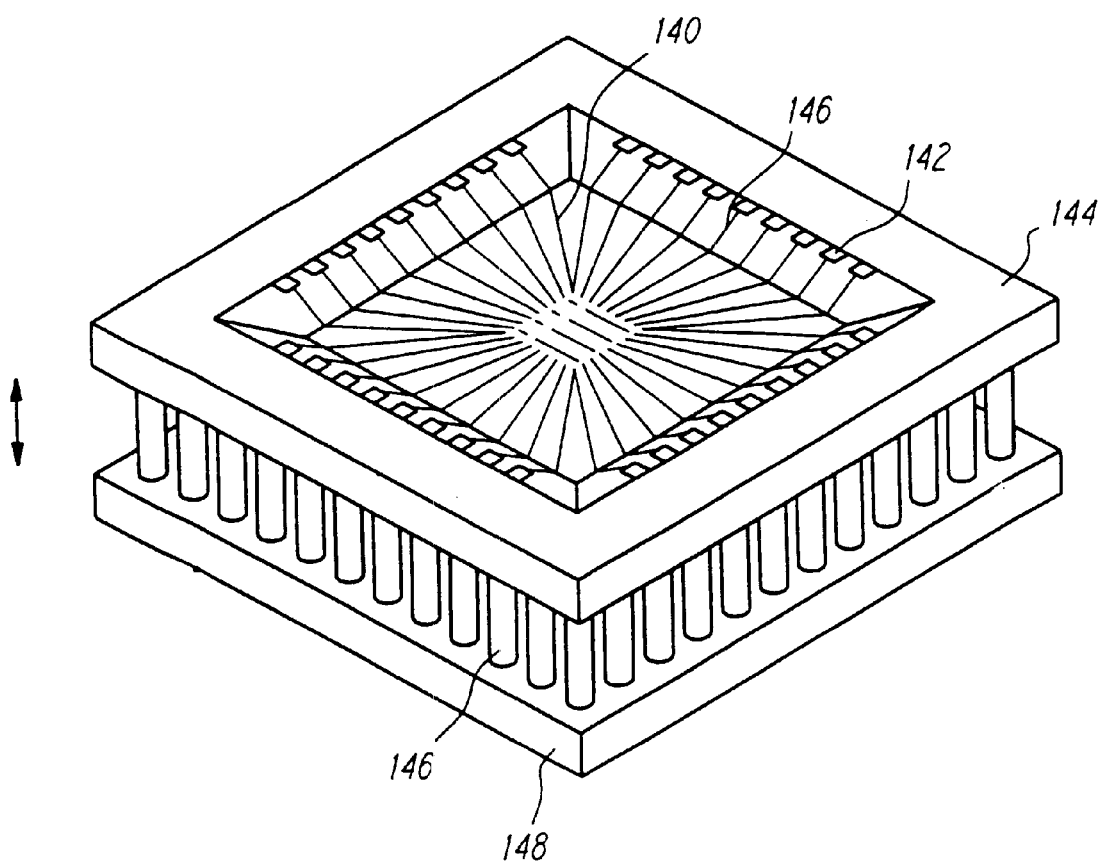
FIG. 10 shows a perspective view of the APEX system mounted in a mating carrier.

FIG. 10 shows a perspective view of a mounting system for an active, programmable matrix system. A system 140 may be formed on a chip using a structure such as that shown in FIGS. 3 and 4. The chip 140 is connected via bonding wires 146 between the contact pads (FIG. 3) and the chip carrier 144 connection pads 142. The chip carrier 144 preferably includes individual pins 147 which provide electrical connection via the pads 142 to the bonding wire 146 onto the chip 140. The pins 147 mate with receptacle 148 which is in turn connected to the control system.

Figure 17:
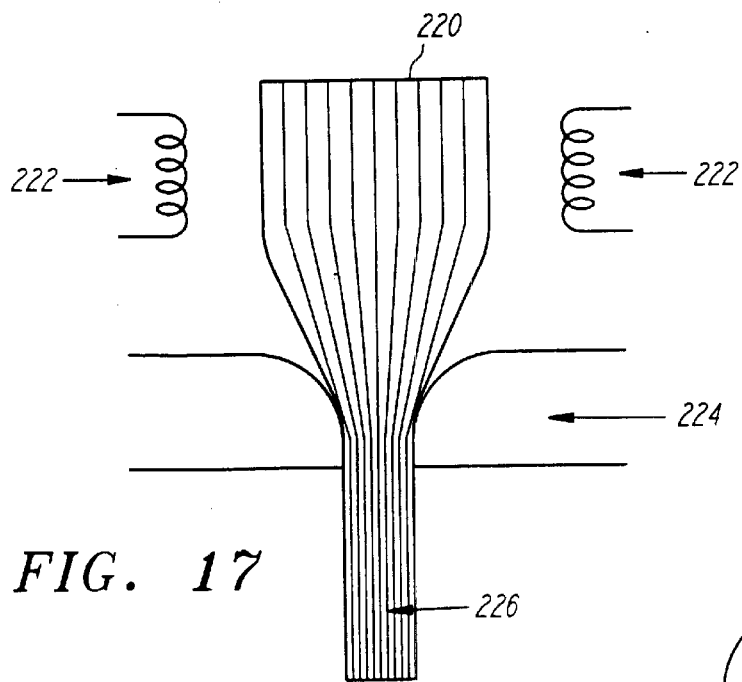
FIG. 17 shows a cross-sectional view of a capillary array manufacturing system and apparatus.
Figure 18:
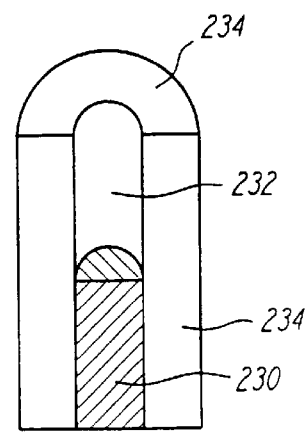
FIG. 18 shows a perspective view of a micro-location of a concentric structure.

Active, programmable matrices of micro-locations can also be formed from capillary tubes. FIG. 17 shows a system and product formed therefrom. Capillary tube matrices are formed by stacking capillary tubes in arrays 220 of arbitrary geometry, or by melting by heater 222 and drawing, such as by die 224, these arrays 220 into an adherent and integral unit 226. Alternatively, solid rods composed of two different materials arranged about each other concentrically can be used instead of capillary tubes. FIG. 18 shows such a structure in perspective. Here, the material that composes the inner core 230 is etched out from the outer material 234 selectively to form a hole 232 that goes partially or all the way through the device. Alternatively, the inner core may be etched in such a way as to form a controlled porousity glass.

Individual capillary tubes can be addressed by wires inserted into the capillary tube, or by affixing the capillary tube matrix to a complimentary matrix of lithographically formed electrodes. Additionally, the inner cores of the solid rods may be formed from a conducting material. Electrical contact can be made with the inner core material by affixing the solid rod matrix to a complimentary matrix of electrodes, or by lithographically forming electrodes on the solid rod matrix.

The capillary tubes and etched solid rods are filled with an appropriate material to form a permeation layer. The surface of the permeation layer can be functionalized with specialized attachment chemistry.

An alternative method to electrophoretic transport is to use convective mass transport to transport material to microlocations. One device that can accomplish this is a rotating disk. Here convection is achieved by the hydrodynamic shear forces present at boundary between the spinning disk and the solution. Fluid flows straight onto the surface from the bulk solution. A matrix of electrode pads can be attached to a spinning disk, or each electrode in the matrix can be attached to a separate disk. In the latter case, each electrode can be addressed selectively by convective mass transport. After the pads are addressed by convective mass transport, the electrode can be used to remove unwanted material using electrophoretic transport.

A preferred process for forming an active, programmable matrix system is described in FIGS. 11A–G. A semiconductor 150, preferably p-type, test grade silicon, has a thick (10,000 Å) oxide 152 formed upon it.

Figure 11A:
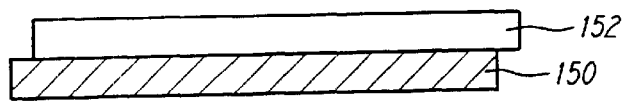
FIGS. 11A–G show process steps in device fabrication.
Figure 11B:
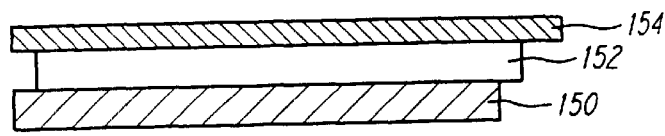
Figure 11C:
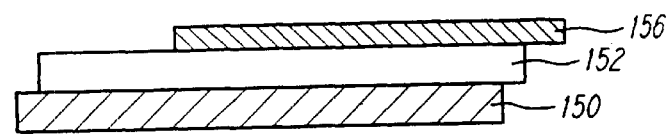

FIG. 11B shows a metal layer 154 formed on the oxide layer 152. Preferably, the metal is chosen from the group consisting of: aluminum, gold, platinum, paladium, titanium, titanium/tungsten. Semiconducting polysilicon may also be used in place of the metal. FIG. 11C shows patterned aluminum 156 formed upon the oxide layer 152. The metal may be patterned by any conventional lithographic technique, such as photolithography.

Figure 11D:
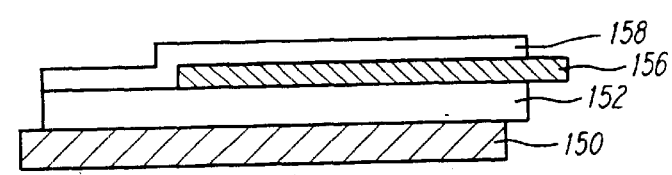
Figure 11E:
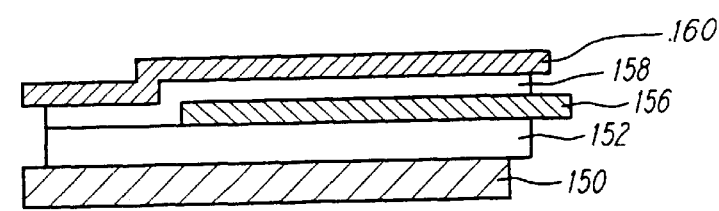
Figure 11F:
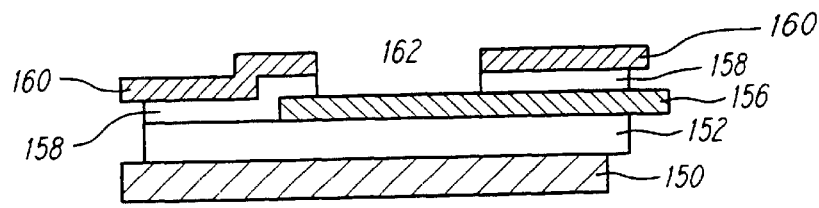

FIG. 11D shows the structure of FIG. 11C with an overcoat of glass, such as TEOS. The TEOS is preferably formed by PECVD techniques. Preferably, the glass is formed at a relatively high temperature, such as 475° C. to promote adhesion to the metal layer 156. The TEOS layer 158 is then overcoated with a nitride layer 160. The nitride layer 160 and TEOS layer 158 are preferably etched in the region above the patterned electrode region 156. This forms a window 162 permitting direct contact to the patterned electrode 156.

Figure 11G:
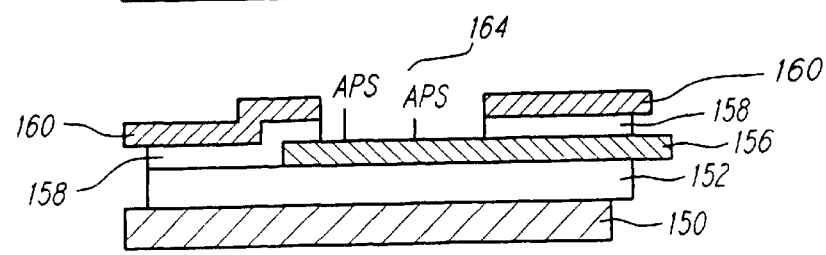

FIG. 11G shows the result of exposing the overall structure to aminopropylsilene (APS). The APS 164 adheres to the patterned metal layer 156 and not to the nitride layer 160. The APS layer serves as the attachment layer for DNA capture probes.

Figure 12:
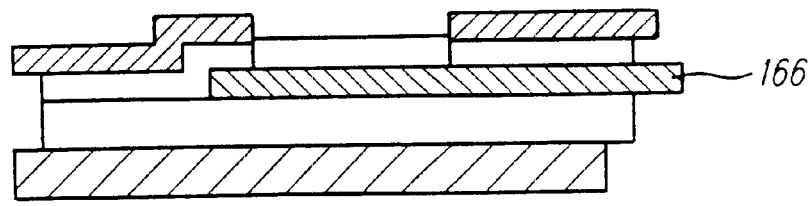
FIG. 12 shows a fabricated device utilizing a polysilicon structure in cross-section.

FIG. 12 shows an alternative structure in which polysilicon is used in lieu of normal metal contacts. The structure is similar to that of FIG. 11F but includes a polysilicon layer 166 in lieu of the aluminum layer 56. The sequence of preferred steps is as follows. First, the semiconductor, preferably p-type, test grade silicon is oxidized with a thick (10,000 Å) oxide. A conductive polysilicon layer, preferably a polysilicon doped 5,000 Å thick layer is formed. The polysilicon is then patterned, preferably by photolithography using a wet etch. Next, a glass layer, such as PECVD deposited TEOS is formed. A layer approximately 3,000 Å formed at 475° C. is preferred for improved adhesion. The glass layer is then patterned, again, preferably with photolithographic techniques using a wet etch. A metal layer is then formed over the surface, preferably by sputtering aluminum to a thickness of 3,000 Å. The metal is then patterned, again preferably photolithographically, with a wet etch. Next, a nitride layer is formed, preferably via PECVD at 70° C. to a thickness of 3,000 Å. Next a via is formed photolithographically using a wet etch so as to contact the electrode.

Figure 13:
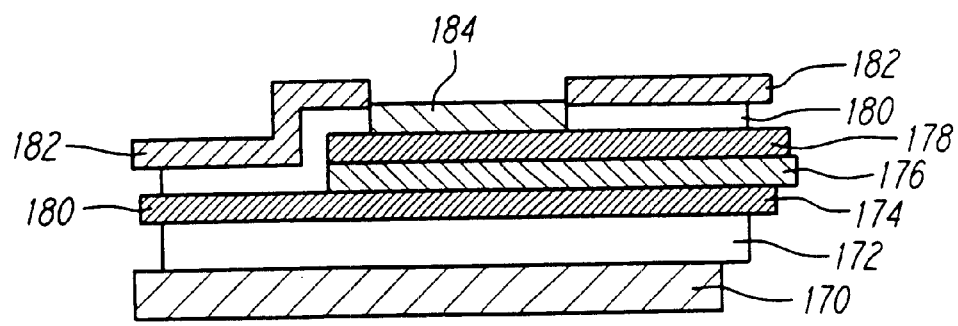
FIG. 13 shows a fabricated device utilizing adhesion enhancing layers in cross-section.

FIG. 13 shows a structure having improved adhesion of metal conductor to underlying insulating layers through the use of an intermediate adhesive metal such as titanium tungsten. A semiconductor 170, preferably silicon, has disposed thereon an oxide layer 172. An intermediate electrode layer 176, formed of a conductive metal such as gold or aluminum, is sandwiched between titanium tungsten 174 and 178. Adhesive metal layer 178 contacts the external electrode 184, preferably formed of platinum. A glass layer 180, such as formed from TEOS, underlies a external nitride coating 182.

Figure 14:
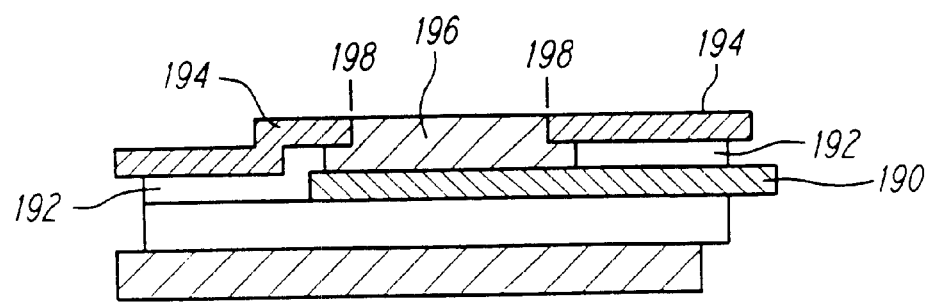
FIG. 14 shows a device having an enlarged reservoir space above the electrode.

FIG. 14 shows a cross-sectional view of an improved electrode arrangement. An electrode 190 is disposed adjacent to an insulator 192, preferably an oxide. A nitride layer 194 overlies the insulator layer 192. Preferably, the nitride layer 194 is undercut such that the insulating layer 192 is set back from the edge 198 of the nitride layer. A reservoir 196 is thereby defined, having a larger volume than a similar structure without the undercut region.

The structure illustrated in FIG. 14 is used to hold mechanically a plug of material that forms a permeation layer. The overhanging layer captures the permeation layer. This design can-be generalized to an arbitrary number of overhanging layers, so as to form an arrangement such as a beehive shape of decreasing concentric circles, or to have varying radii of concentric disk apertures.

The permeation layer (e.g., layer 14 of FIG. 2) may be formed from materials such as, but not exclusive to, carbon chain polymers, carbon-silicon chain polymers, carbon-phosphorous chain polymers, carbon-nitrogen chain polymers, silicon chain polymers, polymer alloys, layered polymer composites, interpenetrating polymer materials, ceramics, controlled porosity glass, materials formed as sol-gels, materials formed as aero-gels, materials formed as hydro-gels, porous graphite, clays or zeolites.

Permeation layers separate the binding entities from the surface of the electrode. Micro-locations have been created using microlithographic and micro-machining techniques. Chemical modification of the surface of the micro-locations and of polymer layers over the microlocations have been used to create specialized attachment sites for surface functionality.

Mesh type permeation layers involve random arrangements of polymeric molecules that form mesh like structures having an average pore size determined by the extent of cross-linking. We have demonstrated the formation of mesh type permeation layers using several polymerizable formulations containing acrylamide as a monomer. We have used triethylene glycol diacrylate, tetraethylene glycol diacrylate and N, N'-Methylene-bi-sacrylamide as cross-linking agents. Poly-1-lysine with molecular weights of 330 kilodaltons and 25 kilodaltons was mixed into the acrylamide/copolymer formulation to provide a means for attaching specialized functionality to the surface of the permeation layer. The mixture was cast onto the surface of the microlocation. It was then photopolymerized by ultraviolet light. In some cases, AuCl4 was added as a photoinitiator. The polymer formulations were cast from water and the non-aqueous solvents, methanol, tetrahydrofuran, acetonitrile, acetone, and mixtures of these solvents.

DNA capture probe was attached to the surface of the permeation layer by a Schiff base reaction between an oxidized ribonucleoside attached to the DNA capture probe and the primary amine of the poly-1-lysine. This provides evidence of covalent attachment of special functionality to the surface of the permeation layer.

An oxidized DNA capture probe was brought to a surface micro-location by electrophoretic transport. The capture probe was labeled with a fluorescent marker. This demonstrates the ability to address a micro-location by electrophoretic transport.

An oxidized capture probe with a fluorescent marker attached was attracted to the surface of the permeation layer at a micro-location by electrophoretic transport. The permeation layer was removed from the micro-location by mechanical means. No evidence of the presence of the fluorescently labeled capture probe was observed. This demonstrates the ability of the permeation layer to protect the DNA from the electrode surface.

The maximum DC current density that was attained at a gold micro-location, which was not modified with a permeation layer, before bubbles due to water hydrolysis appeared was 8 milliampheres/cm2. The maximum DC current density that was attained at a gold micro-location, which was modified by an acrylamide-based permeation layer, before bubbles due to water hydrolysis appear was 40 milliampheres/cm2. This demonstrates the ability of the permeation layer to raise the maximum accessible current density before bubbles form due to water hydrolysis.

An ionomer sandwich permeation layer is formed from one or more lamina of polyelectrolytes. The polyelectrolyte layers may have the same charge, different charge, or may be charge mosaic structures.

A two layer ionomer sandwich layer was formed from a base layer of a perfluorinated sulfonic acid polyelectrolyte (Nafion) and an upper layer of poly-1-lysine. The base Nafion layer was cast onto a micro-location and allowed to dry. This base layer was then exposed to a 1% by weight aqueous solution of poly-1-lysine. The cationic lysine-based polymer adsorbed strongly to the anionic Nafion base layer. The poly-1-lysine layer allowed the attachment of an oxidized DNA capture probe to the surface of the permeation layer by a Schiff base reaction. The Nafion base layer is anionic and is perm-selective toward negative ions such as DNA.

Figure 15:
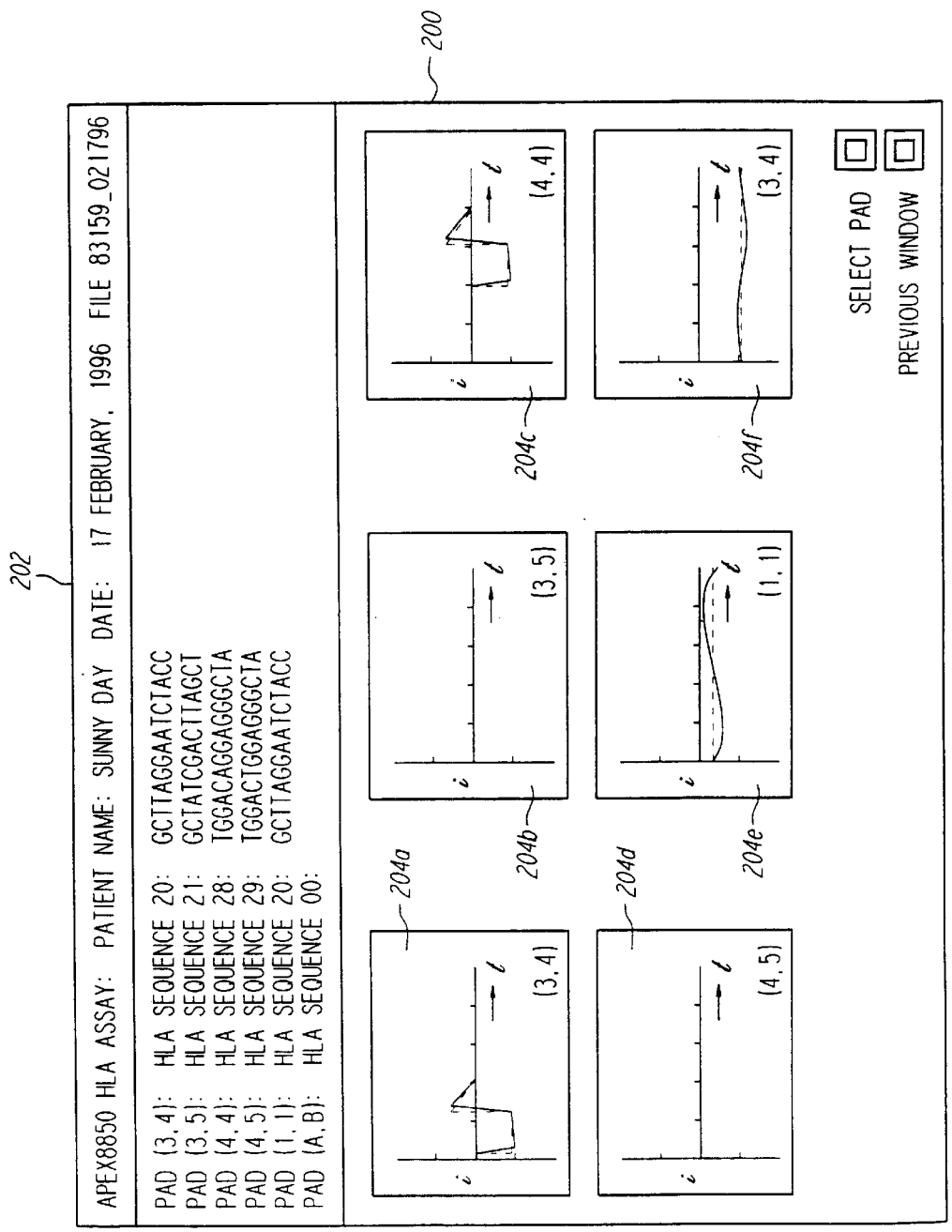
FIG. 15 shows user displays for various voltage and current regimes.

FIG. 15 shows examples of the graphical user interface. Window 200 shows an overall view of the display. Identification information 202 is provided. The various pads of the active, programmable matrix system are identified in a rectangular coordinate system. The displays 204 each show the electrical parameter, such as current or voltage for particular pads. Box 204A shows the current as a function of time for a pad, (3,4), wherein the current varies as a function of time, changing directions during the course of the application. Box 204B shows a pad, (3,5), having no applied current during the time shown. Box 204C shows a time varying current for pad (4,4), wherein that current is delayed with respect to time relative to the pad (3,4) reported in Box 204A. Sox 204D shows a pad, (4,5), with no applied current as a function of time. Box 204E shows a pad, (1,1), for which the voltage has a constant, negative DC value. Box 204F shows the voltage as a function of time for a pad, (3,4) having a more negative DC value. In all cases, the boxes show the programmed current or voltage as a dotted line, and the measured current or voltage as a solid line.

In addition to the preferred embodiment of the invention and the alternatives described above, several more alternatives are possible. For example, the electric field that gives rise to ion migration may be modu lated in time as long as a DC bias voltage or current is applied simultaneously. The use of an AC signal superimposed on a DC bias voltage or current can achieve three things, 1) minimize the background due to nonspecifically bound DNA, 2) provide a means of electronic stringency control where the control variable is the frequency of the alternating current or voltage, 3) provide a means of aligning DNA molecules spatially.

Many alternatives to the detection of hybridized DNA by fluorescence exist. Most of the alternative techniques also involve modification of capture or target or reporter DNA probes with reporter groups that produce a detectable signal. A few of these techniques based on purely physical measurements do not require reporter groups. These alternative techniques are cata logued as follows: (1) Linear Optical Methods including fluorescence, time modulated fluorescence, fluorescence quenching modulation, polarization selective fluorescence, absorption, specular reflectance, changes in index of refraction, ellipsometry, surface plasmon resonance detection, chemiluminescence, speckle interferometry and magneto-optic Kerr effect; (2) Nonlinear Optical Methods including second harmonic generation, third harmonic generation, parametric mixing, optical heterodyne detection, phase conjugation, soliton damping and optical Kerr effect; (3) Methods Based on Thermal Effects including differential scanning calorimetry, multifrequency differential scanning calorimetry, and differential thermal analysis; (4) Methods Based on Mass Changes including crystal microbalances, cantilever microbalances, surface acoustic waves and surface Love waves; (5) Electrochemical Methids including amperometry, coulometry, voltammetry, electrochemiluminescence, charge transfer in donor-acceptor complexes and surface impedance spectroscopy; and (6) Radioactivity Detection Methods using labeled groups.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

We claim:

1. A controlled addressable, programmable electronic matrix device system having a plurality of individually addressable electrodes, comprising:
   a power supply,
   a user input system for receiving user input and generating an output corresponding thereto,
   a controller adapted to receive the output from the input system and provide output including control signals utilized to generate independent electronic environments at the electrodes of the matrix device, the control signals including information relating to at least one parameter selected from the group consisting of:
   polarity, the presence or absence of a connection between the power supply and an individual electrode, and the amount of current or potential supplied to the individual electrode,
   an interface adapted to connect the output of the controller to the matrix device, and
   an active, programmable electronic matrix device, the matrix device comprising:
      a plurality of contact pads for contacting the interface and receiving the control signals,
      a substrate, the substrate supporting the plurality of individually addressable electrodes, wherein the plurality of individual addressable electrodes have a permeation layer disposed thereon,
      biological capture probes disposed attached to the permeation layer for interacting with the specific binding entities;
   and an illumination source operatively positioned to provide radiation to the active matrix device.

2. The control system of claim 1 wherein a circuit element is located proximate to said addressable electrode.

3. The control system of claim 1 wherein the power supply is a regulated power supply.

4. The control system of claim 1 wherein the power supply is a sourced current generator.

5. The control system of claim 1 wherein the power supply comprises a waveform generator.

6. The control system of claim 1 wherein the circuit element includes a relay.

7. The control system of claim 1 wherein the circuit elements include a relay to provide selective connection from the power supply to the electrodes.

8. The control system of claim 1 wherein the circuit elements include a relay adapted to change the polarity of the output of the power supply.

9. The control system of claim 1 wherein the circuit elements include a relay to provide selective connection to either a first level or second level of a signal.

10. The control system of claim 9 wherein the signal is a predetermined voltage level.

11. The control system of claim 9 wherein the signal comprises current at a predetermined level.

12. The control system of claim 1 wherein the control signals include digital signals.

13. The control system of claim 1 wherein the control signals include analog signals.

14. The control system of claim 4 wherein the sourced current generator provides multiple sources of current.

15. The control system of claim 14 wherein the multiple sources of current include different levels of current.

16. The control system of claim 14 wherein the multiple sources of current include current waveforms.

17. The control system of claim 1 wherein the controller comprises a computer.

18. The control system of claim 1 wherein the controller is microprocessor based.

19. The control system of claim 1 further including an output system for providing information to the user.

20. The control system of claim 1 wherein the output system includes a display.

21. The control system of claim 1 further including a detection system, said illumination source being under control of said controller.

22. The control system of claim 1 wherein the said user instructions include an indication of polarity information for at least one said addressable electrode.

23. The control system of claim 1 wherein said controller comprises circuit elements integrated into an underlying semiconductor support.

* * * * *